United States Patent [19]
Helfer

[11] Patent Number: 5,405,520
[45] Date of Patent: Apr. 11, 1995

[54] CONNECTORS FOR ELECTROPHORESIS DEVICE

[75] Inventor: Joel N. Helfer, Chesire, Conn.

[73] Assignee: Eastman Kodak Company, Rochester, N.Y.

[21] Appl. No.: 188,261

[22] Filed: Jan. 27, 1994

[51] Int. Cl.6 .................. G01N 27/26; G01N 27/447
[52] U.S. Cl. ............................... 204/299 R; 204/182.8
[58] Field of Search ............. 204/299 R, 182.8, 182.7

[56] References Cited

U.S. PATENT DOCUMENTS

| | | | |
|---|---|---|---|
| 2,802,188 | 8/1957 | Badders | 439/325 |
| 3,391,383 | 7/1968 | Antes | 439/331 |
| 3,819,505 | 6/1974 | Parent et al. | 204/299 R |
| 3,873,433 | 3/1975 | Seidel et al. | 204/182.8 |
| 4,130,471 | 12/1978 | Grunbaum | 204/182.8 |
| 4,234,400 | 11/1980 | Kaplan et al. | 204/182.8 |
| 4,284,491 | 8/1981 | Vesterberg | 204/299 R |
| 4,576,702 | 5/1986 | Peck et al. | 204/299 R |
| 4,830,725 | 5/1989 | Berninger et al. | 204/299 R |
| 5,242,568 | 9/1993 | Ehr et al. | 204/299 R |

Primary Examiner—John Niebling
Assistant Examiner—John S. Starsiak, Jr.
Attorney, Agent, or Firm—Dana M. Schmidt

[57] ABSTRACT

An electrophoresis device wherein a banana plug for connection to external power is mounted on a cover, and the cover and frame of the device together provide a switch for connecting and disconnecting electrically, the wiring of the inside of the device, and the banana plug, the switch being openable solely by vertically raising the cover, to minimize jolting forces delivered, upon connect or disconnect, to samples inside.

6 Claims, 3 Drawing Sheets

CONNECTORS FOR ELECTROPHORESIS DEVICE

FIELD OF INVENTION

This invention relates to an electrophoresis receptacle having improved electrical connectors for contacting banana plugs therein.

BACKGROUND OF THE INVENTION

Electrophoresis devices are known wherein a housing frame is provided to enclose two electrodes separated by a bridge element using a gel or other separating medium. Each end is provided with an electrical conductor such as an uncovered wire, and this conductor extends along the inside of the housing frame to a connector such as a banana plug at opposite ends of the wire, e.g., as shown in U.S. Pat. No. 4,576,702. External electrical power is applied to or removed from the housing frame by connecting or disconnecting electrical wires at the banana plugs. Although the plugs are shown in the '702 patent as pointing vertically upward, they also have been oriented instead along a horizontal axis. The plugs preferably are accessible only through openings in a cover as shown in the '702 patent, providing a safety feature which prevents opening the cover without disconnecting power.

Whatever the orientation of the banana plugs, such a method of connecting and disconnecting power is disadvantageous because the friction - fit of banana plugs requires some force to be applied when the plugs are connected or disconnected (prior to accessing samples in the device). This force in turn is transmitted back to the electrophoresis housing frame, and tends to undesirably disturb the electrophoresis gel and the samples contained therein. Yet, such disconnect is imperative to protect the user from a possible short upon accessing the samples inside the housing frame.

It has been a problem, therefore, prior to this invention, to provide a method of and apparatus for disconnecting the banana plugs of the electrophoresis device, without disturbing the electrophoresis gel samples inside.

SUMMARY OF THE INVENTION

I have constructed electrical connectors for such banana plugs that solve the aforementioned problem.

More specifically, there is provided an electrophoresis device having a non-jarring electrical connect or disconnect, the device comprising a frame for the electrophoresis device, the frame including a wire positioned to apply current to an electrophoresis gel in the device, a cover for and removably mounted on the frame, the cover including a banana plug for connection to an exterior source of electricity, and connecting means for removably connecting the wire to the banana plug, the connecting means comprising a conductive strip and a conductor, one of the strip and the conductor being mounted on the cover electrically connected to the banana plug, and the other being mounted on the frame electrically connected to the wire, the strip and the conductor having a mutually mating configuration such that the strip engages and disengages the conductor in a vertical plane by lowering and raising, respectively, the cover, whereby jarring of the frame and of the gel therein is minimized.

Therefore, it is an advantageous feature of the invention that an electrophoresis device is provided with electrically connective and disconnective banana plugs, which when connected or disconnected, minimize or eliminate forces being transmitted back to the frame such as can disturb samples inside.

Other advantageous features will become apparent upon reference to the attached drawings, when read in light of the Description of the Preferred Embodiments.

DESCRIPTION OF THE PREFERRED EMBODIMENTS

In the following description, the invention is described in connection with preferred embodiments, in which the frame of the electrophoresis device has a particular horizontal configuration and the banana plugs are oriented on a horizontal axis, when used. Additionally, the invention is also useful if the frame, including the cover, has altered configurations, or if the banana plugs are non-horizontally oriented, or if connectors other than banana plugs are used.

Figure 1:
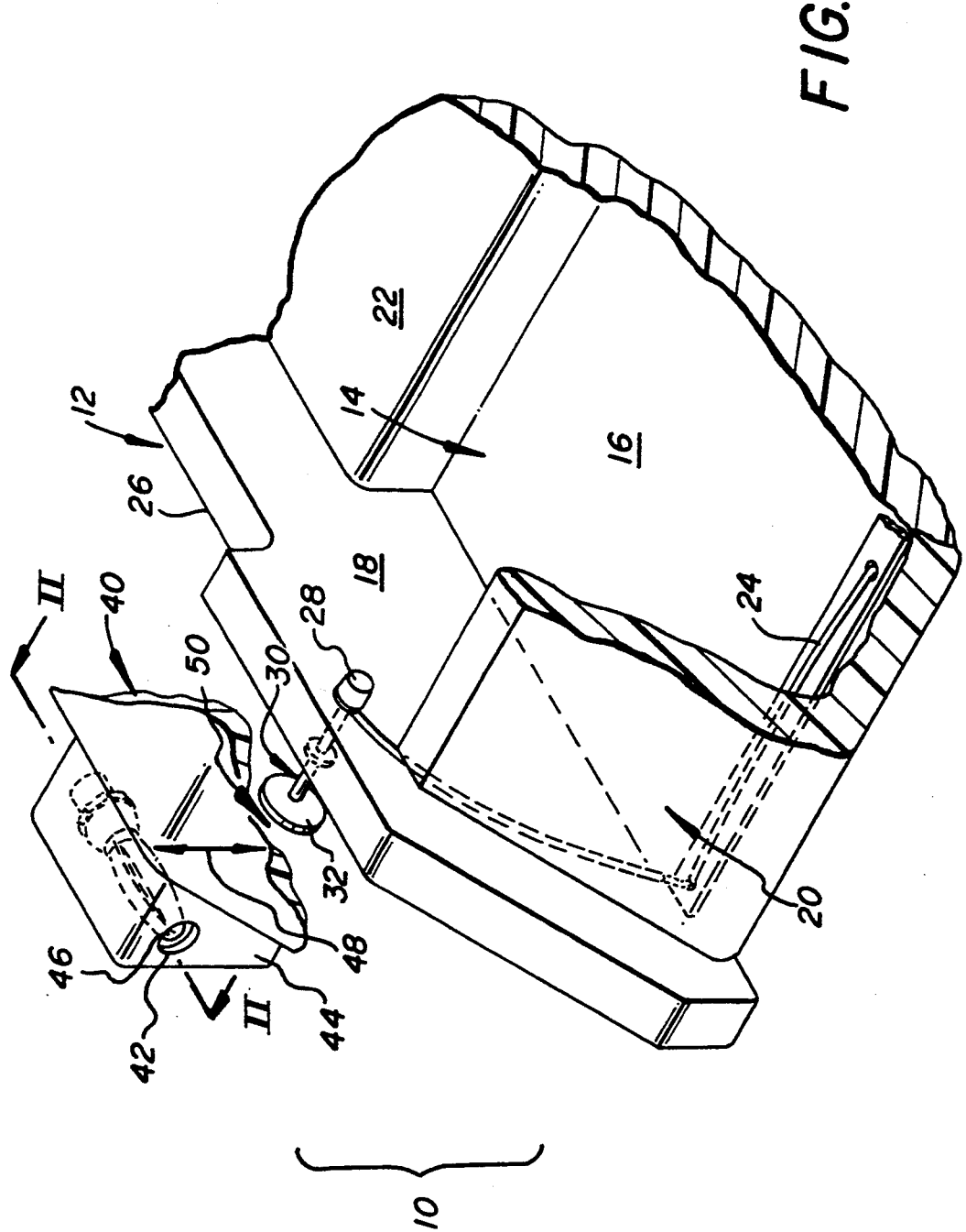
FIG. 1 is a fragmentary, exploded isometric view of a device constructed with the invention.

An electrophoresis device 10 of the invention can have any frame construction 12 in any configuration, FIG. 1, wherein a first liquid compartment 14 is defined by a bottom wall 16, side walls 18 and 20, and a step-up bridge 22. For example, the configuration of said '702 patent can be used. As is conventional, an exposed wire 24 runs along an edge of this compartment, and extends in insulated form within a groove along side wall 18 to a conductor 30 which exits to outside surface 26 of wall 18. Nut 28 can be used for the connection.

Also conventional is a cover 40 that normally sits on the frame to enclose electrophoresis samples. An opening 42 is provided in a portion 44 of the wall of cover 40 to allow access to a banana plug 46 for hook-up of electrical power.

In accordance with the invention, plug 46 is mounted on and as a part of the cover 40, and an intermediate switch 50 is disposed between plug 46 and frame 12 with a construction that permits connection and disconnection by only the vertical movement of the cover, arrow 48.

Figure 2:
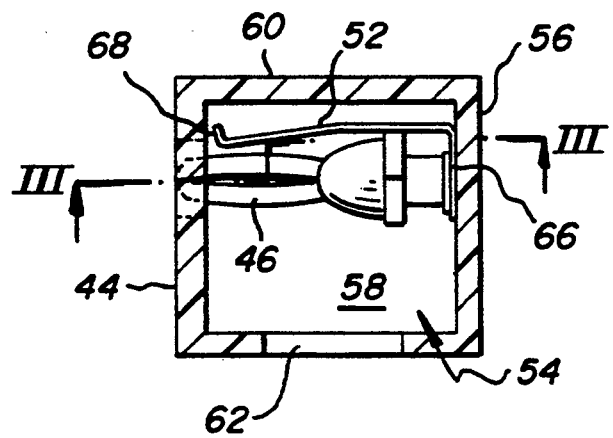
FIG. 2 is an elevational view in section taken generally along the line II—II of FIG. 1 and showing a first embodiment.

More specifically, switch 50 has two mating poles, one being a disc 32 on conductor 30 on frame 12, and the other being a strip 52 on cover 40. Preferably, strip 52 and plug 46 are inside a protective well 54 comprising, FIG. 2, a front and back wall portion 44 and 56, an outside wall 58, and a top wall 60, leaving the underside open at slot 62. The dimensions of slot 62 are limited to those that will only admit disc 32 to the interior of portion 44, for obvious safety reasons. Strip 52 is electrically connected to plug 46, and is configured to connect and disconnect physically by vertical motion with respect to disc 32. In this first embodiment, this configuration comprises a slot 64, FIG. 3, shaped to receive only part of the circumference of disc 32, FIG. 4 defined by, e.g., the arc of angle alpha.

To minimize the force of the physical connection and disconnection, strip 52 is also preferably movable in the vertical direction, by cantilevering it from portion 66 that connects it to plug 46, and by providing a stop surface 68 at the opposite end of the strip. Most preferably, it is spring-biased at its cantilevered connection downwardly.

Figure 3:
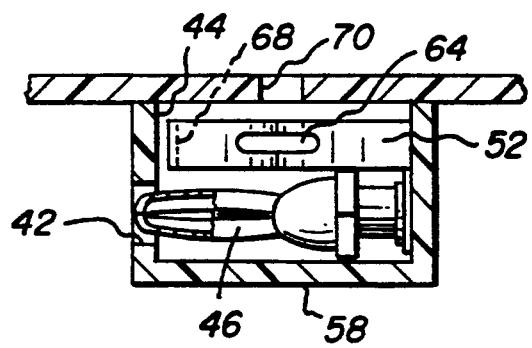
FIG. 3 is a fragmentary section view taken generally along the line III—III of FIG. 2.
Figure 4:
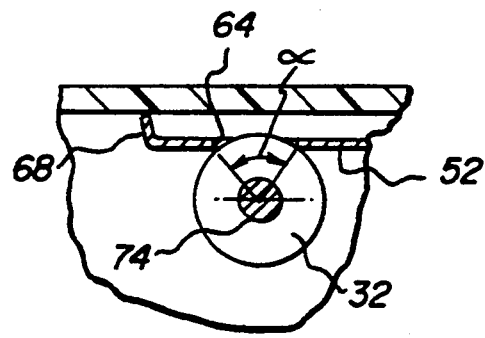
FIG. 4 is a fragmentary elevational view in section, similar to that of FIG. 2, but adding the conductor of the frame to show its contact with the strip (the banana plug having been omitted for clarity)

To allow only vertical connection of disc 32 with slot 64, a vertical slit 70, FIG. 3, is provided in wall 72 of cover 40 that aligns with the shaft 74 of conductor 30, FIG. 1.

Figure 5:
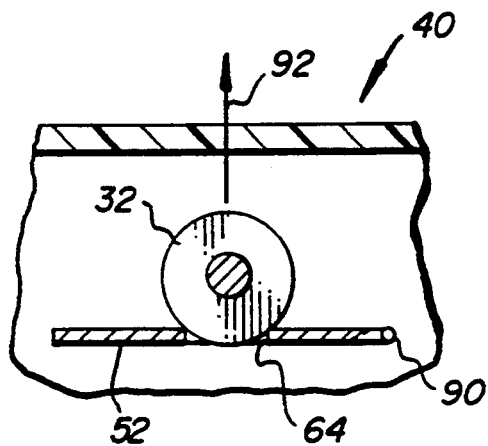
FIG. 5 is a view similar to that of FIG. 4, but showing a second embodiment in which the disc-like conductor is on the cover rather than the frame.

It will be readily apparent that disc 32 and strip 52 can be reversed in position, so that disc 32 is secured to the cover and strip 52 is cantilevered from the housing from an end 90 thereof, FIG. 5. The mating of the two parts is similar to that of FIG. 4, i.e., via slot 64 in strip 52, when cover 40 is lowered onto the frame and strip 52. Disconnection occurs only via vertical movement of the cover, arrow 92.

Figure 6:
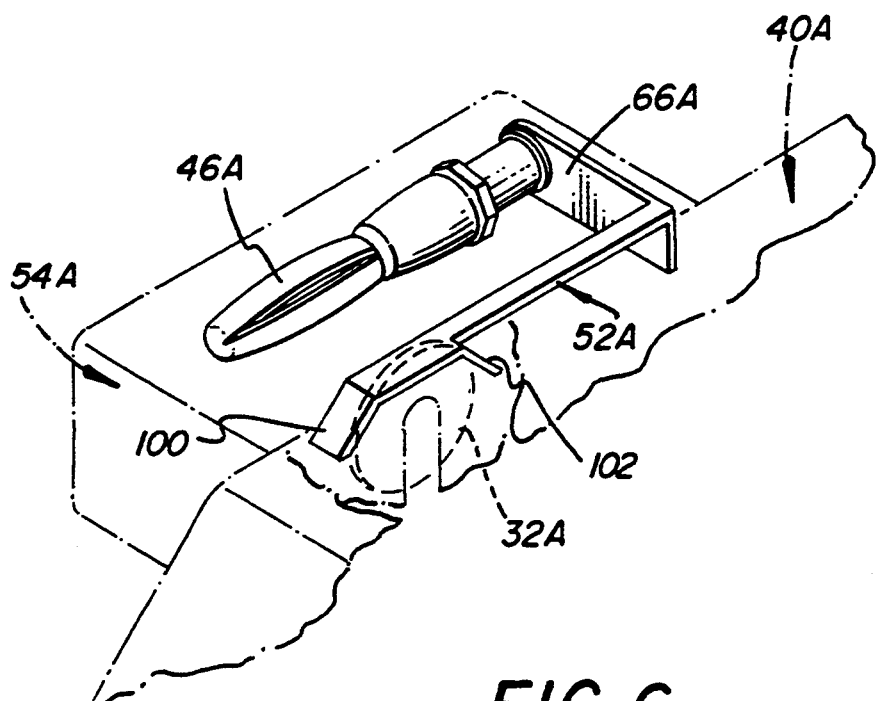
FIG. 6 is a fragmentary isometric view showing a third embodiment in which the strip, instead of being perforated to receive a disc conductor, is a C-shaped leaf for that conductor.

There is no need for the strip to be slotted to vertically engage disc 32, since other configurations will mate and disconnect via a vertical motion, as shown in FIG. 6. Parts similar to those previously described bear the same reference numeral, to which the distinguishing suffix "A" is appended.

Thus, a banana plug 46A is mounted inside a well 54A on cover 40A (shown in phantom), and a disc 32A is affixed to a conductor (not shown) mounted on a frame of the electrophoresis device (also not shown), as before. Plug 46A is electrically connected by metal 66A, as before, to cantilevered strip 52A, inside well 54A. However, unlike the previous embodiment, strip 52A has no slot, but instead is bent with a C-shape the external flanges 100,102 of which will also engage the circumference of disc 32A.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. An electrophoresis device having a non-jarring electrical connect or disconnect, the device comprising a frame for the electrophoresis device, said frame including a wire positioned to apply current to an electrophoresis gel in the device, a cover for and removably mounted on said frame, said cover including a connector for connection to an exterior source of electricity,
    and connecting means for removably connecting said wire to said connector, said connecting means comprising a conductive strip and a conductor, one of said strip and said conductor being mounted on said cover electrically connected to said connector, and the other being mounted on said frame electrically connected to said wire, said strip and said conductor having a mutually mating configuration such that said strip engages and disengages said conductor in a vertical plane by lowering and raising, respectively, said cover,
    whereby jarring of said frame and of the gel therein is minimized.

2. A device as defined in claim 1, wherein said conductor comprises a disc and said strip has a slot therein into which said disc projects for contact when the cover is lowered onto said frame.

3. A device as defined in claim 1, wherein said conductor comprises a disc and said strip is C-shaped to sit on top of said disc for contact when the cover is lowered onto said frame.

4. A device as defined in claim 1, 2 or 3, wherein said strip is on said cover and said conductor is on said frame.

5. A device as defined in claim 1, 2, 3 or 4, and further wherein said strip is cantilevered to move in the vertical direction upon contact with said conductor.

6. An electrophoresis device having a non-jarring electrical connect or disconnect, said device comprising
    a frame for said electrophoresis device, said frame including a wire positioned to apply current to an electrophoresis gel in the device,
    a cover for and removably mounted on said frame, and a connector for connecting said wire to an external source of power,
    said connector being mounted on said cover and said cover and frame together providing a two-pole switch, one pole being connected to said connector and the other to said wire, said switch further comprising a strip and a conductor configured to break electrical contact only by vertically raising said cover from said frame and raising one of said strip and said conductor from contact with the other of said strip and conductor,
    whereby jarring of said frame and of the gel therein is minimized.

* * * * *